(12) United States Patent
Levi et al.

(10) Patent No.: US 7,674,935 B2
(45) Date of Patent: Mar. 9, 2010

(54) CRYSTAL FORMS OF O-DESMETHYLVENLAFAXINE

(75) Inventors: Sigalit Levi, Modi'in (IL); Valerie Niddam-Hildesheim, Kadima (IL); Iamas Koltai, Netanya (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 251 days.

(21) Appl. No.: 11/788,034

(22) Filed: Apr. 17, 2007

(65) Prior Publication Data

US 2008/0033051 A1    Feb. 7, 2008

Related U.S. Application Data

(60) Provisional application No. 60/792,801, filed on Apr. 17, 2006, provisional application No. 60/796,739, filed on May 1, 2006, provisional application No. 60/899,166, filed on Feb. 1, 2007, provisional application No. 60/902,418, filed on Feb. 20, 2007, provisional application No. 60/872,955, filed on Dec. 4, 2006, provisional application No. 60/903,988, filed on Feb. 27, 2007.

(51) Int. Cl.
*C07C 211/00* (2006.01)
*A61K 31/135* (2006.01)

(52) U.S. Cl. .................. 564/336; 564/409; 514/648

(58) Field of Classification Search ................. 564/336, 564/409; 514/648
See application file for complete search history.

(56) References Cited

U.S. PATENT DOCUMENTS 4,535,186 A    8/1985    Husbands et al.
6,197,828 B1   3/2001    Jerussi et al.
6,673,838 B2   1/2004    Hadfield et al.
6,689,912 B2   2/2004    Weber
2002/0022662 A1  2/2002  Yardley et al.
2004/0181093 A1  9/2004  Kim et al.
2005/0197392 A1  9/2005  Jerussi et al.
2007/0135449 A1  6/2007  Mahaney et al.

FOREIGN PATENT DOCUMENTS

EP    0 112 669 A2       7/1984
GB    2 173 787 A       10/1986
WO    WO 00/59851 A1    10/2000
WO    WO 02/064543 A2    8/2002
WO    WO 03/000652 A1    1/2003
WO    WO 03/048104 A1    6/2003
WO    WO 2005/049560 A2  6/2005
WO    WO 2007/011594 A2  1/2007
WO    WO 2007/067501 A1  6/2007
WO    WO 2007/071404 A1  6/2007
WO    WO 2007/120923 A1 10/2007
WO    WO2007/147564     12/2007
WO    WO 2008/013995    1/2008
WO    WO 2008/015584 A2  2/2008

OTHER PUBLICATIONS

Klamerus, K.J. et al., "Introduction of the Composite Parameter to the Pharmacokinetics of Venlafaxine and its Active O-Desmethyl Metabolite," J. Clin. Phavmacol. 32:716-724 (1992).
International Search Report of Application PCT/US07/009560, dated Nov. 26, 2007.
Yardley, John P., et al., 2-Phenyl-2-(1-hydroxycycloalkyl)ethylamine Derivatives: Synthesis and Antidepressant Activity, J. Med. Chem. (1990) 33, pp. 2899-2905, XP000891765.
Third Party Observation received on Jul. 30, 2009 at the EPO for EP Patent Application No. 07755729.6.

*Primary Examiner*—Shailendra Kumar
(74) *Attorney, Agent, or Firm*—Kenyon & Kenyon LLP (57) ABSTRACT

Methods for preparing crystalline forms of O-desmethylvenlafaxine are described.

31 Claims, 4 Drawing Sheets

CRYSTAL FORMS OF O-DESMETHYLVENLAFAXINE

CROSS REFERENCE TO RELATED APPLICATIONS

The present application claims the benefit of the following U.S. Provisional Patent Application Nos. 60/792,801, filed Apr. 17, 2006; 60/796,739, filed May 1, 2006; 60/899,166, filed Feb. 1, 2007; 60/902,418, filed Feb. 20, 2007; 60/872,955, filed Dec. 4, 2006; and 60/903,988, filed Feb. 27, 2007. The contents of these applications are incorporated herein by reference.

FIELD OF INVENTION

The present invention is directed to a crystalline forms of O-desmethylvenlafaxine and methods of preparation thereof.

BACKGROUND OF THE INVENTION

Venlafaxine, (±)-1-[2-(Dimethylamino)-1-(4-ethyoxyphenyl)ethyl]cyclo-hexanol, having the following formula I, is the first of a class of anti-depressants. Venlafaxine acts by inhibiting re-uptake of norepinephrine and serotonin, and is an alternative to the tricyclic anti-depressants and selective re-uptake inhibitors.

formula I

O-desmethylvenlafaxine, chemically named 4-[2-(dimethylamino)-1-(1-hydroxycyclohexyl)ethyl]phenol and having the following formula II formula II $C_{16}H_{25}NO_2$
Mol. Wt.:263.38 is a major metabolite of venlafaxine and has been shown to inhibit norepinephrine and serotonin uptake. Klamerus, K. J. et al., "Introduction of the Composite Parameter to the Pharmacokinetics of Venlafaxine and its Active O-Desmethyl Metabolite", *J. Clin. Phavmacol.* 32:716-724 (1992).

O-desmethylvenlafaxine and processes for preparation thereof are described in U.S. Pat. Nos. 6,197,828 and 6,689,912, and in US 2005/0197392, which are incorporated herein by reference.

Venlafaxine base can be used as a starting material in the preparation of O-desmethylvenlafaxine, as demonstrated in U.S. Pat. No. 6,689,912, U.S. Pat. No. 6,197,828, WO 03/048104 and US 2005/0197392.

Polymorphism, the occurrence of different crystal forms, is a property of some molecules and molecular complexes. A single molecule, like O-desmethylvenlafaxine, may give rise to a variety of crystalline forms having distinct crystal structures and physical properties like melting point, x-ray diffraction pattern, infrared absorption fingerprint, FTIR spectrum, and solid state NMR spectrum. One crystalline form may give rise to thermal behavior different from that of another crystalline form. Thermal behavior can be measured in the laboratory by such techniques as capillary melting point, thermogravimetric analysis ("TGA"), and differential scanning calorimetry ("DSC"), which have been used to distinguish polymorphic forms.

The difference in the physical properties of different crystalline forms results from the orientation and intermolecular interactions of adjacent molecules or complexes in the bulk solid. Accordingly, polymorphs are distinct solids sharing the same molecular formula yet having distinct advantageous physical properties compared to other crystalline forms of the same compound or complex.

One of the most important physical properties of pharmaceutical compounds is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. Different crystalline forms or polymorphs of the same pharmaceutical compounds can and reportedly do have different aqueous solubilities.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

There is a need in the art for polymorphic forms of O-desmethylvenlafaxine.

SUMMARY OF THE INVENTION

In one embodiment, the present invention provides a method of preparing a crystalline form of O-desmethylvenlafaxine characterized by X-ray powder diffraction reflections at about: 12.1, 13.2, 15.9 and 20.4 degrees two theta ±0.2 degrees two theta by crystallization from a solvent selected from the group consisting of: ethanol, tetrahydrofuran (THF), isopropyl alcohol (IPA) and a mixture of IPA and water. Preferably, the method of preparing a crystalline form of O-desmethylvenlafaxine by crystallization from ethanol also comprises washing with an appropriate washing liquid. More preferably, the washing liquid is heptane.

In another embodiment, the present invention provides a crystalline form of O-desmethylvenlafaxine, characterized by X-ray powder diffraction reflections at about: 13.1, 16.2, 19.8, 20.6 and 22.2 degrees two theta ±0.2 degrees two theta.

In another embodiment, the present invention provides a crystalline form of O-desmethylvenlafaxine, characterized by X-ray powder diffraction reflections at about: 12.2, 13.3, 18.1 and 19.7 degrees two theta ±0.2 degrees two theta.

In another embodiment, the present invention provides pharmaceutical compositions comprising at least one of the above crystal forms of O-desmethylvenlafaxine and a pharmaceutically acceptable excipient.

In another embodiment, the present invention provides a process for preparing a pharmaceutical composition comprising at least one of the crystalline forms of O-desmethylvenlafaxine of the present invention and a pharmaceutically acceptable excipient.

In yet another embodiment, the present invention provides pharmaceutical formulations comprising at least one of the crystalline forms of O-desmethylvenlafaxine prepared according to the processes of the present invention, and a pharmaceutically acceptable excipient.

In another embodiment, the present invention provides a process for preparing pharmaceutical formulations comprising at least one of the crystalline forms of O-desmethylvenlafaxine prepared according to the processes of the present invention, and a pharmaceutically acceptable excipient.

In another embodiment, the present invention provides a method of treating a patient comprising administering to a patient in need thereof a therapeutically effective amount of the above crystalline forms of O-desmethylvenlafaxine.

DETAILED DESCRIPTION OF THE INVENTION

In one embodiment, the present invention provides a method of preparing a crystalline form of O-desmethylvenlafaxine characterized by X-ray powder diffraction reflections at about: 12.1, 13.2, 15.9 and 20.4 degrees two theta ±0.2 degrees two theta by crystallization from a solvent selected from the group consisting of: ethanol, tetrahydrofuran (THF), isopropyl alcohol (IPA) and a mixture of IPA and water.

When ethanol is used as a crystallization solvent, preferably, absolute ethanol is used.

The crystalline form may then be recovered by any method known in the art, such as washing the particles. Preferably, the particles crystallized from ethanol are washed with an appropriate washing liquid. More preferably the washing liquid is a $C_5$-$C_8$ hydrocarbon, such as heptane.

The method of the present invention for preparing a crystalline form of O-desmethylvenlafaxine characterized by X-ray powder diffraction reflections at about: 12.1, 13.2, 15.9 and 20.4 degrees two theta ±0.2 degrees two theta comprises; a) combining O-desmethylvenlafaxine starting material and a solvent selected from the group consisting of ethanol, tetrahydrofuran (THF), isopropyl alcohol (IPA) and a mixture of IPA and water to form a mixture; b) heating the mixture at a temperature and for a sufficient period to obtain dissolution, preferably at about 50° C. to about 100° C., more preferably at 60° C. to about 80° C.; and c) recovering the crystalline O-desmethylvenlafaxine.

Preferably, the heating step comprises refluxing the mixture for a sufficient time to effect complete dissolution of the O-desmethylvenlafaxine starting material.

In this process of the present invention heating may comprise evaporating the solvent.

Figure 1:
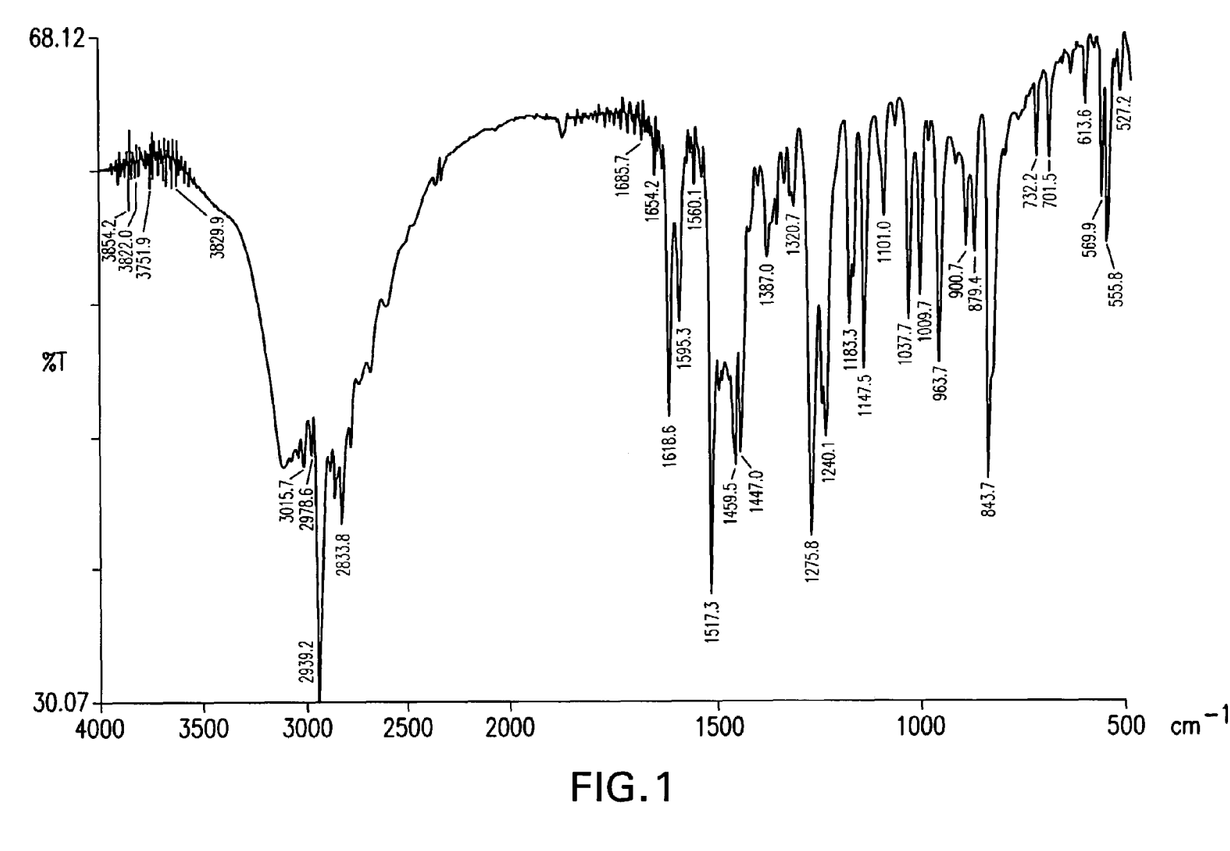
FIG. 1 shows a FTIR spectrum of form A of O-desmethylvenlafaxine.
Figure 2:
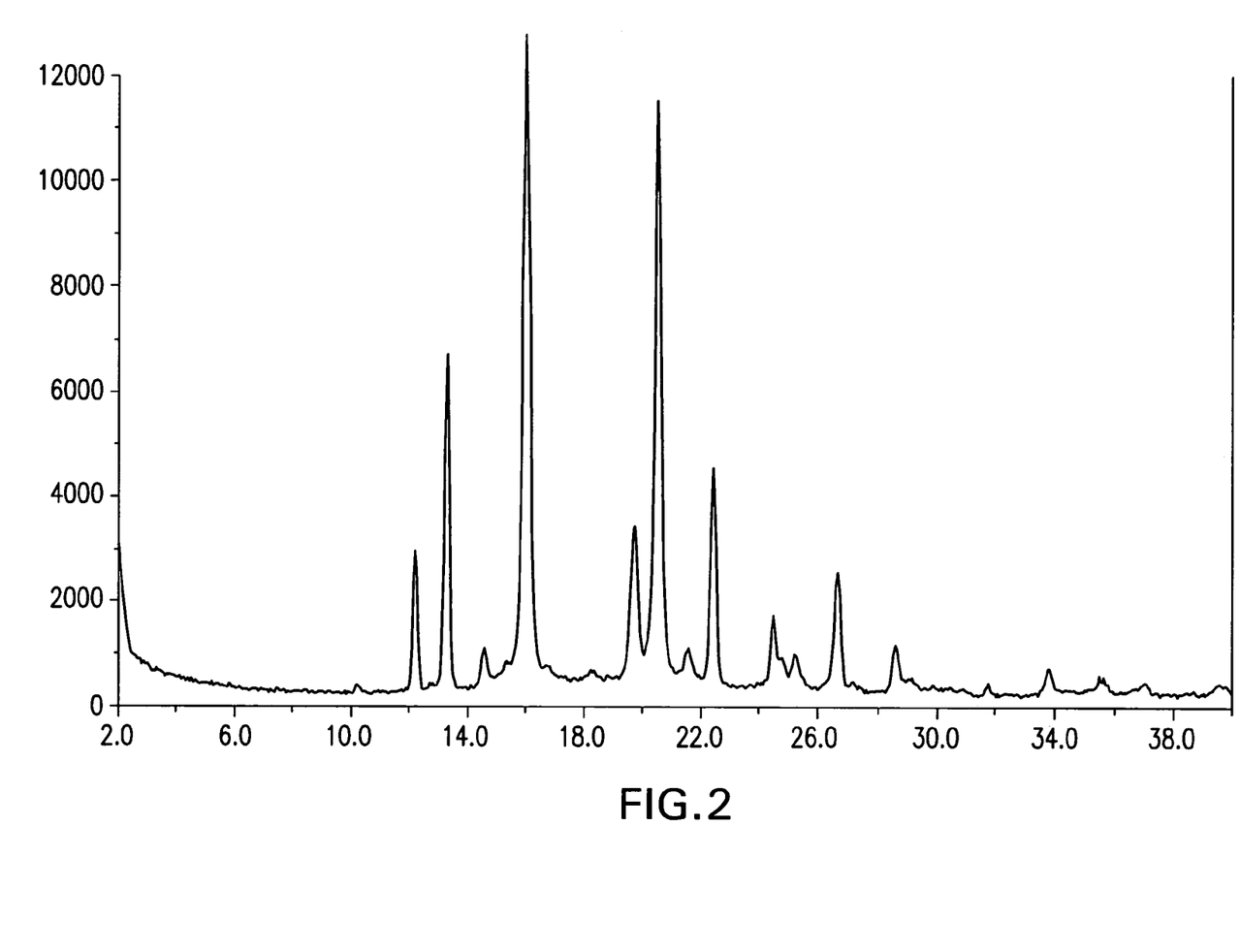
FIG. 2 shows a PXRD for form A of O-desmethylvenlafaxine.

The crystalline form of O-desmethylvenlafaxine characterized by X-ray powder diffraction reflections at about 12.1, 13.2, 15.9, and 20.4 degrees two theta ±0.2 degrees two theta is denominated form A. Crystalline O-desmethylvenlafaxine form A may be further characterized by a FTIR spectrum having peaks at about 844, 1276, 1517, and 1619 cm$^{-1}$. A FTIR spectrum of crystalline O-desmethylvenlafaxine form A may further contain peaks at about 1148, 1240, 1447, 1460, 2834, and 2939 cm$^{-1}$, or is substantially as depicted in FIG. 1.

The O-desmethylvenlafaxine starting material can be obtained by any method known in the art, such as the one described in U.S. Pat. No. 6,197,828, which is incorporated herein by reference. Preferably, the O-desmethylvenlafaxine is obtained in a process comprising demethylating venlafaxine base as described in the following scheme:

In another embodiment, the present invention provides a crystalline form of O-desmethylvenlafaxine, characterized by X-ray powder diffraction reflections at about: 13.1, 16.2, 19.8, 20.6 and 22.2 degrees two theta ±0.2 degrees two theta. This form is denominated Form C.

Form C can be further characterized by X-ray powder diffraction peaks at about 12.2, 15.6 and 26.2 degrees two-theta, ±0.2 degrees two-theta. A powder x-ray diffraction diagram of Form C is given in FIG. 3.

In another embodiment, the present invention provides a process for the crystallization of O-desmethylvenlafaxine Form C from a high boiling point solvent. The starting material for this crystallization to obtain O-desmethylvenlafaxine Form C may be a O-desmethylvenlafaxine salt, preferably the starting material for crystallization of Form C from toluene is the succinate salt of O-desmethylvenlafaxine, more preferably O-desmethylvenlafaxine succinate characterized by X-ray powder diffraction peaks at about 13.18, 14.04, 14.35, 14.66, 16.68, 17.67, 19.24, 25.13, and 31.78, (Form II).

The O-desmethylvenlafaxine succinate starting material can be obtained by any method known in the art, such as the one described in U.S. Pat. No. 6,673,838, which is incorporated herein by reference.

As used herein, the term "high boiling point solvent" refers to a solvent having a boiling point higher than about 100° C. Preferably, the high boiling point solvent is selected from the group consisting of: toluene, dimethylformamide (DMF), dimethylsulfoxide (DMSO), N-methyl-2-pyridone, N-methyl-2-pyrrolidone, 1-methyl-2-pyrolidinone (NMP) and dimethylacetamide (DMA). More preferably, the high boiling point solvent is toluene.

Crystallization of this form of O-desmethylvenlafaxine may be carried out by dissolving O-desmethylvenlafaxine in a high boiling point solvent by heating a suspension of O-desmethylvenlafaxine starting material with a high boiling point solvent, cooling the obtained solution to a temperature of about 15° C. to about 30° C. and maintaining the cooled solution at this temperature for a period of time, followed by recovering the crystalline O-desmethylvenlafaxine. Preferably the suspension is heated to a temperature of about 100° C. to about 110° C., more preferably to about reflux. The obtained solution is preferably cooled to a temperature of about 15° C. to about 30° C., more preferably to about room temperature, and preferably maintained at this temperature for a period of at least about 30 minutes, preferably about 30 minutes to about 1 hour.

In a preferred method, the reaction occurs while stirring at about room temperature for at least about 30 minutes, preferably about 30 minutes to about 1 hour.

Form C may then be recovered by any methods known in the art.

In one embodiment, the present invention provides a process for preparing O-desmethylvenlafaxine Form C which comprises heating O-desmethylvenlafaxine, followed by cooling the compound.

Preferably, heating is carried out to achieve melting of the compound.

Preferably, the compound is cooled to a temperature of from about 0° C. to about room temperature, more preferably to a temperature of about 5° C. to about 25° C.

The O-desmethylvenlafaxine starting material can be obtained as described above.

In another embodiment, the present invention provides a crystalline form of O-desmethylvenlafaxine, characterized by X-ray powder diffraction reflections at about: 12.2, 13.3, 18.1 and 19.7 degrees two theta ±0.2 degrees two theta. This form is denominated Form D.

Form D can be further characterized by X-ray powder diffraction peaks at about 22.5, 25.3 and 28.7 degrees two-theta, ±0.2 degrees two-theta. A powder x-ray diffraction diagram of Form D is given in FIG. 4.

In another embodiment, the present invention provides a process for preparing O-desmethylvenlafaxine Form D which comprises suspending O-desmethylvenlafaxine in N-methylpyrrolidinone (NMP). Preferably, the O-desmethylvenlafaxine is suspended at a temperature of about 15° C. to about 30° C., more preferably at a temperature of about room temperature. The suspension may be maintained at such temperature for a period of about 24 hours to about 48 hours, more preferably for about 32 hours to about 48 hours, to obtain crystalline O-desmethylvenlafaxine.

The O-desmethylvenlafaxine starting material is preferably crystalline. More preferably, the O-desmethylvenlafaxine starting material is Form A of O-desmethylvenlafaxine, as defined above.

Preferably, the O-desmethylvenlafaxine is wetted with 2-3 drops of NMP and is preferably maintained at room temperature for about 48 hours, to obtain O-desmethylvenlafaxine Form D.

In another embodiment, the present invention provides pharmaceutical compositions comprising at least one of the above crystal forms of O-desmethylvenlafaxine or a combination thereof and a pharmaceutically acceptable excipient.

In another embodiment, the present invention provides a process for preparing a pharmaceutical composition comprising at least one of the crystalline forms of O-desmethylvenlafaxine of the present invention and a pharmaceutically acceptable excipient.

In yet another embodiment, the present invention provides pharmaceutical formulations comprising at least one of the crystalline forms of O-desmethylvenlafaxine prepared according to the processes of the present invention, and a pharmaceutically acceptable excipient.

In another embodiment, the present invention provides a process for preparing pharmaceutical formulations comprising at least one of the crystalline forms of O-desmethylvenlafaxine prepared according to the processes of the present invention, and a pharmaceutically acceptable excipient.

Pharmaceutical compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups, and suspensions. Suitable forms of parenteral administration include an aqueous or non-aqueous solution or emulsion, while for rectal administration, suitable forms for administration include suppositories with hydrophilic or hydrophobic vehicle. For topical administration, the invention provides suitable transdermal delivery systems known in the art, and for nasal delivery, there are provided suitable aerosol delivery systems known in the art.

In addition to the active ingredient(s), the pharmaceutical compositions of the present invention may contain one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease the release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, the active ingredient and any other solid excipients are suspended in a liquid carrier such as water, vegetable oil, alcohol, polyethylene glycol, propylene glycol or glycerin. In such suspension the solid excipients may be either in solution or suspended in the liquid carrier. The active ingredient retains its crystalline structure in such liquid pharmaceutical compositions.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxy toluene, butylated hydroxyanisole, and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate, or sodium acetate.

Selection of excipients and the amounts used may be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages may be conveniently presented in unit dosage form and prepared by any of the methods well known in the pharmaceutical arts.

Dosage forms include solid dosage forms like tablets, powders, capsules, suppositories, sachets, troches, and losenges, as well as liquid syrups, suspensions, and elixirs.

The dosage form of the present invention may be a capsule containing the composition, preferably a powdered or granulated solid composition of the invention, within either a hard or soft shell. The shell may be made from gelatin, and, optionally, contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended, and then further mixed in the presence of a liquid, typically water, that causes the powders to clump into granules. The granulate is screened and/or milled, dried, and then screened and/or milled to the desired particle size. The granulate may then be tableted or other excipients may be added prior to tableting, such as a glidant and/or a lubricant.

A tableting composition may be prepared conventionally by dry blending. For example, the blended composition of the actives and excipients may be compacted into a slug or a sheet, and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

In another embodiment, the present invention provides a method of treating a patient comprising administering to a patient in need thereof a therapeutically effective amount of the above crystalline form of O-desmethylvenlafaxine. Preferably, the patient suffers from a condition which may be treated with a norepinephrine or a serotonin re-uptake inhibitor. Such patient may be suffering from depression.

Having described the invention with reference to certain preferred embodiments, other embodiments will become apparent to one skilled in the art from consideration of the specification. The disclosures of the references referred to in this patent application are incorporated herein by reference. The invention is further defined by reference to the following examples describing in detail the process and compositions of the invention. It will be apparent to those skilled in the art that many modifications, both to materials and methods, may be practiced without departing from the scope of the invention.

EXAMPLES

The XRD diffraction was performed on Scintag X-ray powder diffractometer model X'TRA with a solid state detector. Copper radiation of 1.5418 Å was used. The sample holder was a round standard aluminum sample holder with rough zero background. The scanning parameters were range: 2-40 degrees two-theta; scan mode: continuous scan; step size: 0.05 deg.; and at a rate of 5 deg/min.

Preparation of O-desmethylvenlafaxine

Example 1

A mixture of Venlafaxine (5.7 g, 20.4 mmol) and L-Selectride, 1.0 M solution in THF (61 ml, 61 mmol) was refluxed for about 48 hours. Methanol (30 ml) was added dropwise to the stirred mixture at 0-5° C. (ice/water bath), the mixture was evaporated under reduced pressure and Hydrochloric acid, 5% aq. solution (125 ml) was added to the residue. The mixture was extracted with Ethyl acetate (3×40 ml), an aqueous layer was basified with 21% aq. solution of Sodium hydroxide to pH 11, filtered and washed with Ethyl acetate (3×30 ml) to give a residue (4.0 g).

Preparation of O-desmethylvenlafaxine Crystal Form A

Example 2

5 g of O-desmethylvenlafaxine was crystallized from abs. Ethanol and washed with Heptane (3×30 ml) to give 1.6 g (30.0%) of O-Desmethylvenlafaxine as white crystals with mp 222.2-223° C. and 99.17% purity by HPLC.

Example 3

A 500 ml flask equipped with a condenser and a mechanical stirrer was charged with O-desmethylvenlafaxine base (17.5 g) and IPA (450 ml). The mixture was heated to reflux until complete dissolution. The solution was then slowly cooled to 5° C. and maintained at this temperature for 2 hours. The solid was filtered under reduced pressure and dried overnight under vacuum at 60° C. to get pure O-desmethylvenlafaxine base (15.63, 89.3%). HPLC analysis 99.95%

Example 4

A 100 ml flask equipped with mechanical stirrer was charged with O-desmethylvenlafaxine (1 g) and THF (100 ml) at ambient temperature for 20 minutes. The solution was filtered and evaporated at 40° C. under reduced pressure to get pure O-desmethylvenlafaxine base form A.

Preparation of O-desmethylvenlafaxine Crystal Form C

Example 5

O-desmethylvenlafaxine Succinate (0.5 g, form II) and toluene (7.5 ml) were put in 25 ml flask with magnetic stirrer. The suspension was heated to reflux until almost complete dissolution. The fine particles present were decanted and the clear solution was cooled to room temperature over 30 minutes to 1 hour. The solution was stirred at this temperature for 1 hour. The solid that appeared was then filtered under reduced pressure. The wet sample was analyzed by XRD and found to be form C. The solid was dried few hours at 50° C. under vacuum and analyzed by XRD. The solid was found to be form C.

Example 6

0.5 g of O-desmethylvenlafaxine base was heated in a test tube until melting. The melted compound was then cooled to ambient temperature. The compound so-obtained was analyzed by XRD and found to be form C.

Example 7

0.5 g of O-desmethylvenlafaxine base was heated in a test tube until melting. The melted compound was poured into ice-cold water. The compound so-obtained was analyzed by XRD and found to be form C.

Preparation of O-desmethylvenlafaxine Crystal Form D

Example 8

A 100 ml flask equipped with mechanical stirrer was charged with O-desmethylvenlafaxine (1 g) and N-methylpyrrolidinone (3 drops) at ambient temperature over weekend. The solid was then analyzed by XRD and found to be form D.

What is claimed is:

1. A method of preparing a crystalline form of O-desmethylvenlafaxine characterized by X-ray powder diffraction reflections at about 12.1, 13.2, 15.9, and 20.4 degrees two theta ±0.2 degrees two theta comprising crystallization; wherein said crystallization comprises
    a) combining O-desmethylvenlafaxine starting material and a solvent selected from the group consisting of ethanol, tetrahydrofuran (THF), isopropyl alcohol (IPA) and a mixture of IPA and water to form a mixture;
    b) heating the mixture at a temperature of about 50° C. to about 100° C. and for a sufficient period to obtain dissolution; and
    c) recovering the crystalline O-desmethylvenlafaxine.

2. The method of claim 1, wherein the solvent is absolute ethanol.

3. The method of claim 1, wherein the mixture is heated to a temperature of about 60° C. to about 80° C.

4. The method of claim 1, wherein the heating step comprises refluxing for a sufficient time to effect complete dissolution of the O-desmethylvenlafaxine starting material.

5. The method of claim 1, wherein the heating step comprises evaporating the solvent.

6. The method of claim 1, wherein the crystalline form of O-desmethylvenlafaxine is further characterized by a FTIR spectrum having peaks at about 844, 1276, 1517, and 1619 cm$^{-1}$.

7. The method of claim 6, wherein the FTIR spectrum has further peaks at 1148, 1240, 1447, 1460, 2834, 2939 cm$^{-1}$.

8. The method of claim 7, wherein the FTIR spectrum is substantially as depicted in FIG. 1.

9. A crystalline form of O-desmethylvenlafaxine, characterized by X-ray powder diffraction reflections at about: 13.1, 16.2, 19.8, 20.6 and 22.2 degrees two theta ±0.2 degrees two theta.

10. The crystalline form of O-desmethylvenlafaxine of claim 9, further characterized by X-ray powder diffraction reflections at 12.2, 15.6, and 26.2 degrees two theta ±0.2 degrees two theta.

Figure 3:
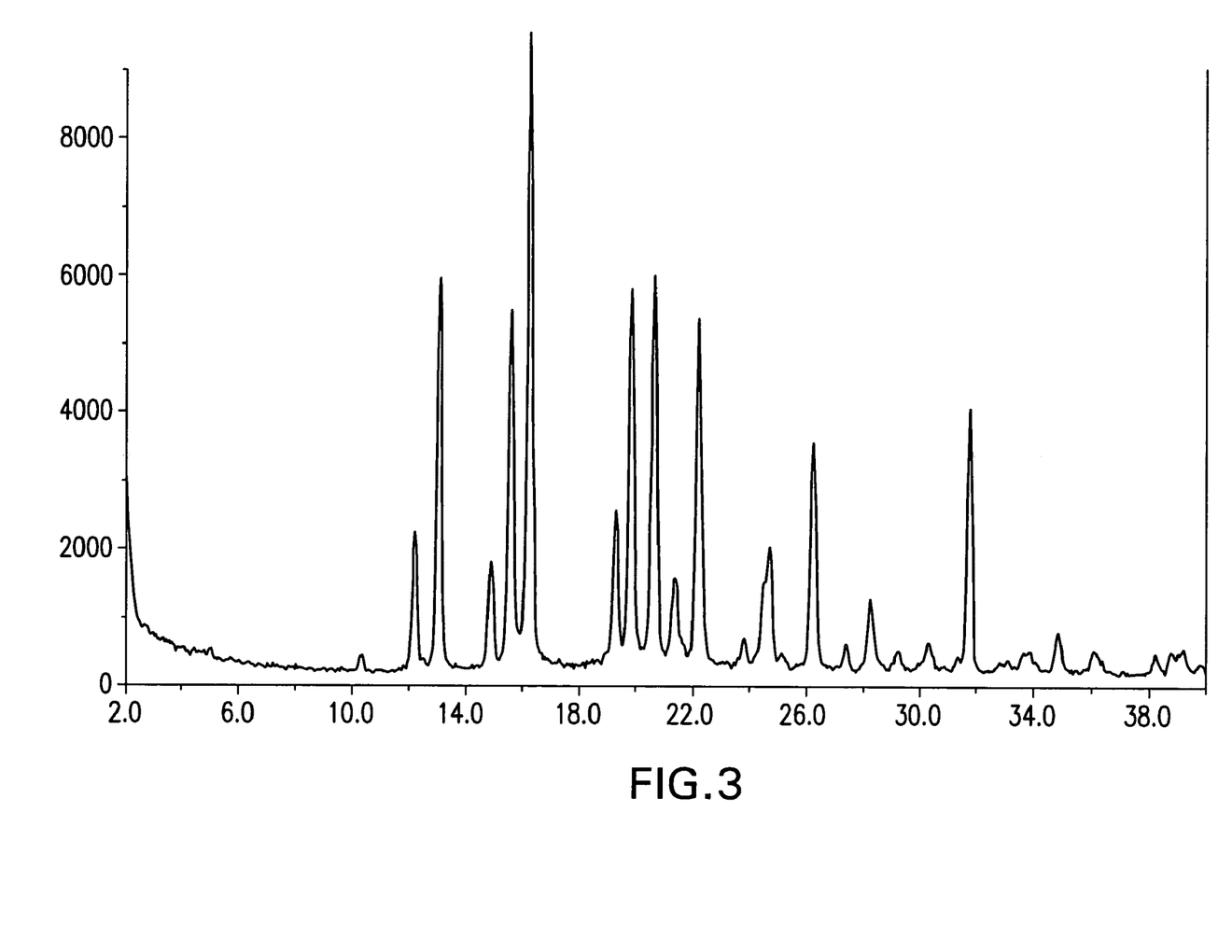
FIG. 3 shows a PXRD for crystalline form C of O-desmethylvenlafaxine.

11. The crystalline form of O-desmethylvenlafaxine of claim 10, further characterized by the powder X-ray diffraction diagram substantially as depicted in FIG. 3.

12. A crystalline form of O-desmethylvenlafaxine, characterized by X-ray powder diffraction reflections at about: 12.2, 13.3, 18.1 and 19.7 degrees two theta ±0.2 degrees two theta.

13. The crystalline form of O-desmethylvenlafaxine of claim 12, further characterized by X-ray powder diffraction reflections at 22.5, 25.3, and 28.7 degrees two theta ±0.2 degrees two theta.

Figure 4:
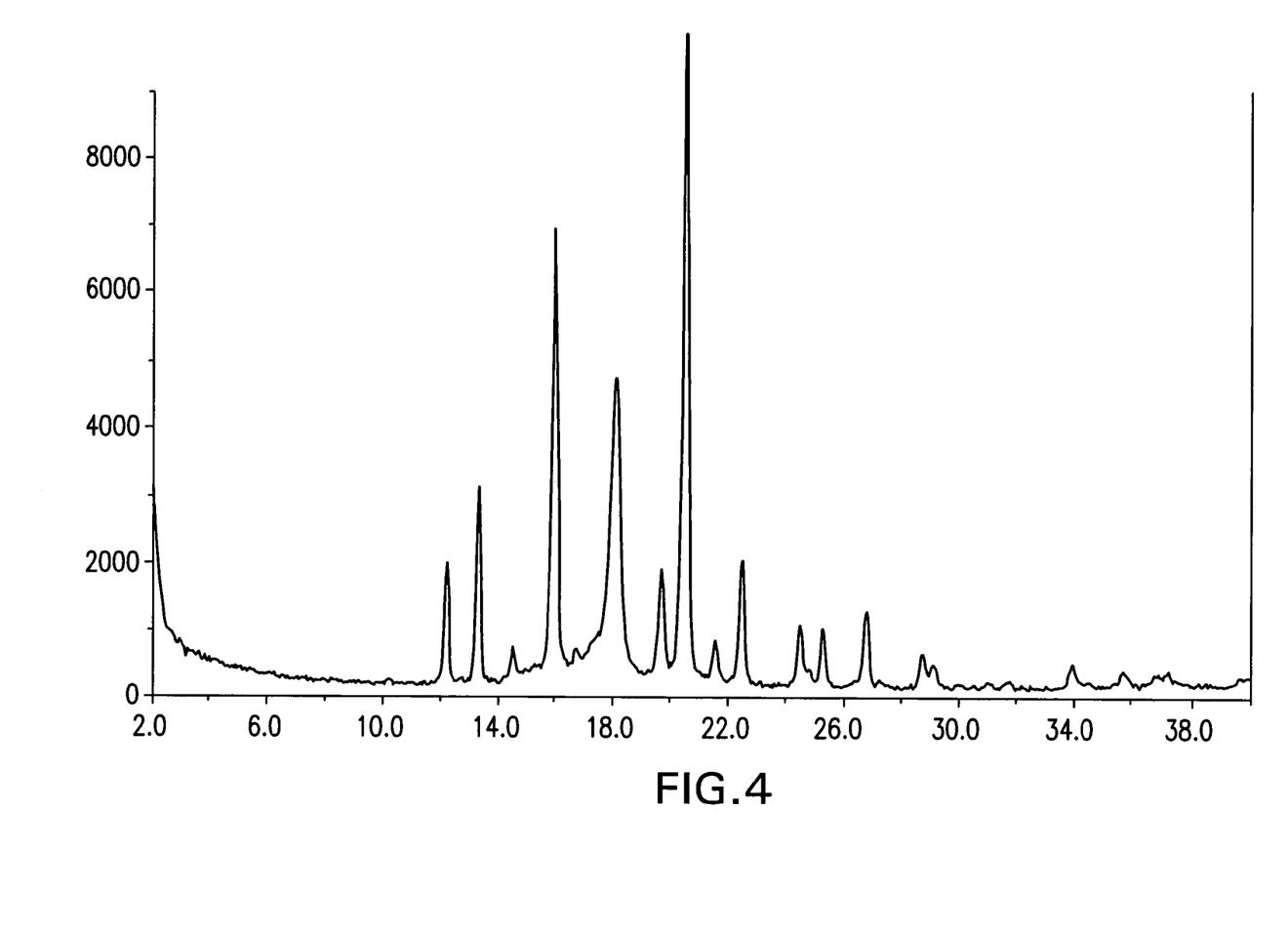
FIG. 4 shows a PXRD for crystalline form D of O-desmethylvenlafaxine.

14. The crystalline form of O-desmethylvenlafaxine of claim 13, further characterized by the powder X-ray diffraction diagram substantially as depicted in FIG. 4.

15. A method of preparing the crystalline form of O-desmethylvenlafaxine of claim 9, comprising crystallizing O-desmethylvenlafaxine from a high boiling point solvent.

16. The method of claim 15, wherein the high boiling solvent is toluene.

17. The method of claim 15, comprises;
a) dissolving O-desmethylvenlafaxine or a salt thereof in a high boiling point solvent by heating a suspension of starting material O-desmethylvenlafaxine in the high boiling point solvent;
b) cooling the solution to a temperature of about 15° C. to about 30° C.;
c) maintaining the cooled solution at a temperature of about 15° C. to about 30° C. for a sufficient time to crystallize O-desmethylvenlafaxine; and optionally
d) recovering crystalline O-desmethylvenlafaxine.

18. The method of claim 17, wherein the suspension is heated to reflux.

19. The method of claim 17, wherein the high boiling point solvent is toluene and the suspension is heated to a temperature 100° C. to 110° C.

20. The method of claim 17, wherein the starting material is a O-desmethylvenlafaxine salt.

21. The method of claim 20, wherein the O-desmethylvenlafaxine salt is the succinate salt of O-desmethylvenlafaxine.

22. The method of claim 17, wherein the solution is cooled to about room temperature.

23. The method of claim 17, wherein the cooled solution is maintained at 15° C. to about 30° C. for a period of at least about 30 minutes.

24. The method of claim 23, wherein the period is about 30 minutes to about 1 hour.

25. A method of preparing the crystalline form of O-desmethylvenlafaxine of claim 9, comprising melting starting material O-desmethylvenlafaxine; and cooling the melted starting material O-desmethylvenlafaxine.

26. The method of claim 25, wherein cooling the heated starting material is to a temperature of about 0° C. to about room temperature.

27. A method of preparing the crystalline form of O-desmethylvenlafaxine of claim 12, comprising suspending O-desmethylvanlafaxine in N-methylpyrrolidinone (NMP) to obtain the crystalline form of O-desmethylvenlafaxine.

28. The method of claim 27, wherein the O-desmethylvenlafaxine is suspended at a temperature of about 15° C. to about 30° C.

29. The method of claim 28, wherein O-desmethylvenlafaxine starting material is wetted with NMP at about room temperature for a period of about 24 to about 48 hours.

30. A pharmaceutical composition comprising the crystalline form of O-desmethylvenlafaxine claim 9, and a pharmaceutically acceptable excipient.

31. A method of treating a patient comprising administering to a patient in need thereof a therapeutically effective amount of the crystalline form of O-desmethylvenlafaxine claim 9.

* * * * *